(12) United States Patent
Chang

(10) Patent No.: US 6,859,285 B1
(45) Date of Patent: Feb. 22, 2005

(54) OPTICAL OBSERVATION DEVICE AND METHOD FOR OBSERVING ARTICLES AT ELEVATED TEMPERATURES

(75) Inventor: Tzyy-Shuh Chang, Ann Arbor, MI (US)

(73) Assignee: OG Technologies, Inc., Ann Arbor, MI (US)

( * ) Notice: Subject to any disclaimer, the term of this patent is extended or adjusted under 35 U.S.C. 154(b) by 447 days.

(21) Appl. No.: 09/630,479

(22) Filed: Aug. 2, 2000

Related U.S. Application Data

(60) Provisional application No. 60/151,565, filed on Aug. 31, 1999.

(51) Int. Cl.[7] .............................................. G01B 11/30
(52) U.S. Cl. ...................... 356/601; 356/237.1; 110/185
(58) Field of Search .......................... 356/237.1, 237.2, 356/237.3, 601–613; 250/330, 222.1; 110/185, 186; 431/10, 12, 13, 75; 382/152; 164/457

(56) References Cited

U.S. PATENT DOCUMENTS

| | | | |
|---|---|---|---|
| 3,187,185 A | * | 6/1965 | Milnes ..................... 250/222.1 |
| 3,727,054 A | | 4/1973 | Herrick .................. 250/83.3 D |
| 3,748,471 A | | 7/1973 | Ross et al. ................... 250/333 |
| 4,118,732 A | | 10/1978 | Ichijima et al. ............. 358/101 |
| 4,183,055 A | | 1/1980 | Burkhardt, Jr. et al. ...... 358/101 |
| 4,237,959 A | | 12/1980 | Yamamoto et al. ............. 164/4 |
| 4,280,137 A | | 7/1981 | Ashida et al. ............... 358/101 |
| 4,319,270 A | | 3/1982 | Kimura et al. ............... 358/106 |
| RE31,166 E | | 3/1983 | Korda ......................... 360/53 |
| 4,408,903 A | | 10/1983 | Baldasarri .................... 374/121 |
| 4,410,787 A | | 10/1983 | Kremers et al. ........ 219/124.34 |
| 4,481,664 A | | 11/1984 | Linger et al. ................... 382/8 |
| 4,578,561 A | | 3/1986 | Corby, Jr. et al. ...... 219/124.34 |
| 4,608,599 A | | 8/1986 | Kaneko et al. .............. 358/113 |
| 4,641,036 A | | 2/1987 | Ohno et al. | |
| 4,649,426 A | | 3/1987 | Bolstad ....................... 358/101 |
| 4,737,614 A | | 4/1988 | Richardson ............ 219/130.01 |
| 4,744,407 A | * | 5/1988 | Fishman et al. ......... 164/155.2 |
| 4,759,072 A | | 7/1988 | Yamane et al. ................ 382/8 |
| 4,795,906 A | | 1/1989 | Adams et al. ............... 250/341 |
| 4,868,649 A | | 9/1989 | Gaudin ....................... 358/101 |
| 4,918,517 A | | 4/1990 | Burgoon ..................... 358/101 |
| 4,996,426 A | | 2/1991 | Cielo et al. .................. 250/330 |
| 5,060,309 A | | 10/1991 | Narita ......................... 359/154 |
| 5,069,005 A | | 12/1991 | Hovland et al. ............... 51/322 |
| 5,139,412 A | * | 8/1992 | Kychakoff et al. ............ 431/12 |
| 5,240,329 A | | 8/1993 | Zinkosky ....................... 374/5 |
| 5,255,088 A | | 10/1993 | Thompson .................. 358/101 |
| 5,281,826 A | | 1/1994 | Ivancic et al. ............ 250/461.1 |
| 5,292,195 A | | 3/1994 | Crisman, Jr. ................... 374/4 |
| 5,294,198 A | | 3/1994 | Schlagheck .................... 374/4 |
| 5,683,181 A | | 11/1997 | Shepard ...................... 374/165 |
| 5,711,603 A | | 1/1998 | Ringermacher et al. ....... 374/5 |
| 5,719,395 A | | 2/1998 | Lesniak ...................... 250/330 |
| 5,781,302 A | | 7/1998 | Grow et al. | |
| 5,834,661 A | | 11/1998 | Nonaka et al. ............... 73/866 |
| 5,995,008 A | * | 11/1999 | King et al. ............ 250/339.15 |

FOREIGN PATENT DOCUMENTS

| | | |
|---|---|---|
| FR | 7704807 | 9/1978 |
| GB | 1441211 A | 6/1976 |
| JP | 2000131 | 5/2000 |

OTHER PUBLICATIONS

"Automated Inspectio of Hot Steel Slabs," by E.T. Tromborg and G.D. Hunter, *ISA Transactions*, vol. 22, No. 3, 1983, pp. 59–69, ISA Research Triangle Park, NC, US.
"VisiBrite Imaging Systems," on http://oxfordlasers.com/bsi/visibrite.htm.

* cited by examiner

*Primary Examiner*—Richard A. Rosenberger
*Assistant Examiner*—Vincent P. Barth
(74) *Attorney, Agent, or Firm*—Dykema Gossett PLLC

(57) ABSTRACT

An optical system for viewing hot objects is disclosed. The system projects electromagnetic radiation to the part surface and detects the reflected portion. Based on wavelength and/or modulation of the applied illumination, the surface characteristics of the part can be observed without interference from self-emitted radiation.

3 Claims, 5 Drawing Sheets

OPTICAL OBSERVATION DEVICE AND METHOD FOR OBSERVING ARTICLES AT ELEVATED TEMPERATURES

This application claims the benefit of U.S. Provisional Application Ser. No. 60/151,565 filed Aug. 31, 1999.

FIELD OF THE INVENTION

The present invention relates generally to methods and devices for optically observing objects at high temperatures, including objects having significant self-emitted radiation.

BACKGROUND OF THE INVENTION

In a number of industries, workers still visually inspect hot, glowing objects with their unprotected eyes. Direct exposure to infrared (IR) radiation, however, could cause physical injury to the workers. Accordingly, in some instances, light shields are worn which attenuate the radiation, thus providing some protection against IR exposure. However, the use of light shields often restricts the workers' mobility. For example, wearing a light shield may restrict their ability to physically interact with other objects that are not glowing, such as tools, controls and the like.

Conventional optical inspection devices have also been used to make observations/inspections of hot objects. For example, the so-called "passive method" utilizes a signal collector, either with CRT tubes, charge-coupled device (CCD) cameras, or IR cameras, to receive the self-emitted radiation from the hot objects. This approach is similar to the use of human vision, with the signal collectors essentially functioning as "eyes". The passive method, however, is subject to a phenomenon known as the "Cavity Radiator Effect." The Cavity Radiator Effect, postulated by Plank in 1900 and proved by Einstein in the early 20th century, can deceive visual observers as to the true nature of the object observed. More specifically, based on this principle, concave surface features of a self-radiating object appear to be nearly perfect black bodies; accordingly, they may be mistaken as convex features. Additionally, the "illumination" is self-emitted and thus often carries unwanted information. Images collected via this passive method are generally not suitable for automatic machine vision applications.

Another prior art approach, the so-called "active method" utilizes external lights that are projected onto the hot object. A camera is used to collect the reflected, as well as the self-emitted radiation from the hot surfaces. In the active method the idea is to overpower the self-emitted radiation with very strong external radiation. In other words, the reflected light is within the spectrum of the predominant self-emitted radiation, but is distinguishable based on its intensity. The external lights can be designed to highlight the surface information of interest such as contour and surface dimples. The external radiation can be provided by various light-generating devices such as high power lamps or lasers.

Several problems, however, are associated with the active approach. First, few light sources exist that can overpower the radiation emitted by an object at 1350° C. Second, the self-emitted radiation still represents a problem: it degrades the signal quality of the reflected radiation. The signal-to-noise ratio (external light/self-emitted light) is typically low unless a very powerful light source is used. Third, these external light sources may be undesirable in the work environment because they are so intense.

Lasers have also been used as a light source to overpower self-emitted radiation from hot objects. Lasers can deliver extremely high power densities to reduce the significance of the self-emitted radiation. For example, a copper-based laser (radiating at 550 nm) has been used to overpower the self-emitted radiation of laser welding pool (temperature at about 3000° C.), which typically radiates from 230 nm to long IR.

Another prior art approach uses YAG lasers (1060 nm) in arc welding (temperature at about 2500° C.), which typically radiates a spectrum of from 275 nm to long IR. However, the use of lasers poses substantial problems. While lasers deliver high power density, the areas illuminated by the laser beams are small. Consequently, raster scanning is typically required when lasers are used as illumination sources. Moreover, these high power lasers are expensive, bulky, and pose various risks. And, in order to operate a laser-based system, the users must be protected with light shields and other protective equipment.

The use of infrared (IR) sensors or cameras in a passive method vision system are also of limited value due to several factors. First, IR sensors/cameras provide significantly less pixel resolution than their CCD counterparts. Second, IR radiation cannot be focused as well as visible light due to its wavelength. Third, using IR sensors/cameras does not solve the problems associated with illumination or the Cavity Radiator Effect previously described.

There have been attempts to use a combination of passive and active methods, but this approach does not resolve the issues posed by the Cavity Radiator Effect and self-emitted radiation.

In the past, the difference between IR and visible light has been the focal point of solving the problems associated with the glare of hot objects. This approach is ill-conceived because a hot object can radiate with both IR and visible light radiation. For instance, steel radiates at 650 nm at 1200° C.; that is, steel can radiate in RED as well as IR. In addition, if the self-emitted radiation is not removed from the collected signal, the noise caused by the self-emitted radiation impairs the system's ability to gather detailed and accurate information about the hot object. The prior art lacks an effective means of removing the self-emitted radiation from the collected signal of a hot object. Finally, it is also believed that none of the devices enabled by the prior art is portable. This fact has limited the utility of such devices for certain applications. A portable device would be desirable for users who need to look at hot objects, but who do not need to take quantitative measurements. The external light sources used in prior art devices are too powerful and/or heavy to be low-risk and portable. In summary, the prior art approaches have been of limited value. The present invention overcomes these problems.

SUMMARY OF THE INVENTION

In one aspect, the present invention provides an optical system for characterizing the surface of a high-temperature object. The optical system has an illumination source which projects electromagnetic radiation toward the high-temperature object (applied EMR). The applied electromagnetic radiation strikes the high-temperature object and is reflected toward an EMR detector along with the self-emitted electromagnetic radiation and any ambient (background) electromagnetic radiation. At least one component of the reflected, applied EMR (which interacts with the surface of the high-temperature object) is selectively detected by the EMR detector. In one aspect, this selectively identifiable, reflected EMR comprises EMR having a wavelength which is determined on the basis of the temperature of the object; that is, based on wavelength it is distinguishable from the predominant self-emitted EMR and background EMR. In this manner, detection of the reflected EMR provides an image of the high-temperature object which simulates the object surface at low temperatures (i.e. below that producing any significant self-emitted EMR).

In another aspect, the component of the reflected, applied EMR which is identified by the detector has a distinctive signature produced by modulating the applied EMR. In this aspect, the optical system of the present invention further includes an EMR modulator.

In still another aspect, the present invention is implemented in a hand-held device.

DESCRIPTION OF THE PREFERRED EMBODIMENTS

Figure 1:
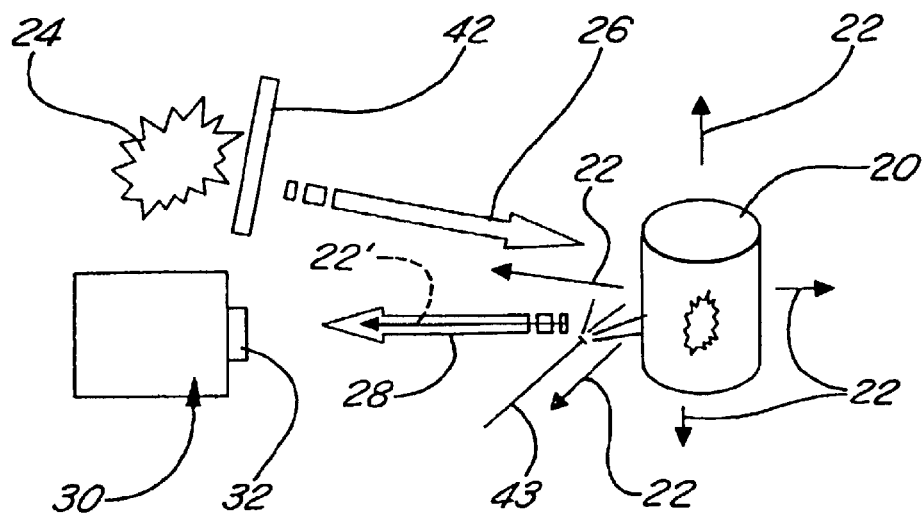
FIG. 1 is a diagram illustrating the present invention.

Referring now to FIG. 1 of the drawings, in one embodiment of the present invention target or object 20 is seen having self-emitted electromagnetic radiation 22. Object 20 will typically comprise a part, for example a carbon steel part, a titanium alloy part, a glass part, or a ceramic part. It will be appreciated that in a number of part fabrication processes, these parts are heated to temperatures in excess of 900° C. It will also be understood that at these high temperatures, these parts emit a substantial amount of radiation which obscures view of the heated part (i.e., a dominant, self-emitted EMR spectrum).

Referring still to FIG. 1 of the drawings, light source 24 is shown which projects electromagnetic radiation 26 toward the surface of part 20. Radiation 26 is the applied illumination. A component of applied illumination 26 is reflected by part 20 and is therefore illustrated in FIG. 1 as reflected illumination 28. It will be noted that in tandem with reflected illumination 28, a portion of self-emitted radiation 22 (shown as 22') and some ambient radiation (not shown) takes the same path as reflected illumination 28.

Reflected illumination 28 (and self-emitted radiation 22') strike detector or sensor 30. As will be explained more fully herein, by distinguishing reflected illumination 28 from self-emitted radiation 22' (and any other "noise" such as ambient radiation) detector 30 can view object 20 as if the part were cool (essentially no self-emitted radiation).

Figure 2:
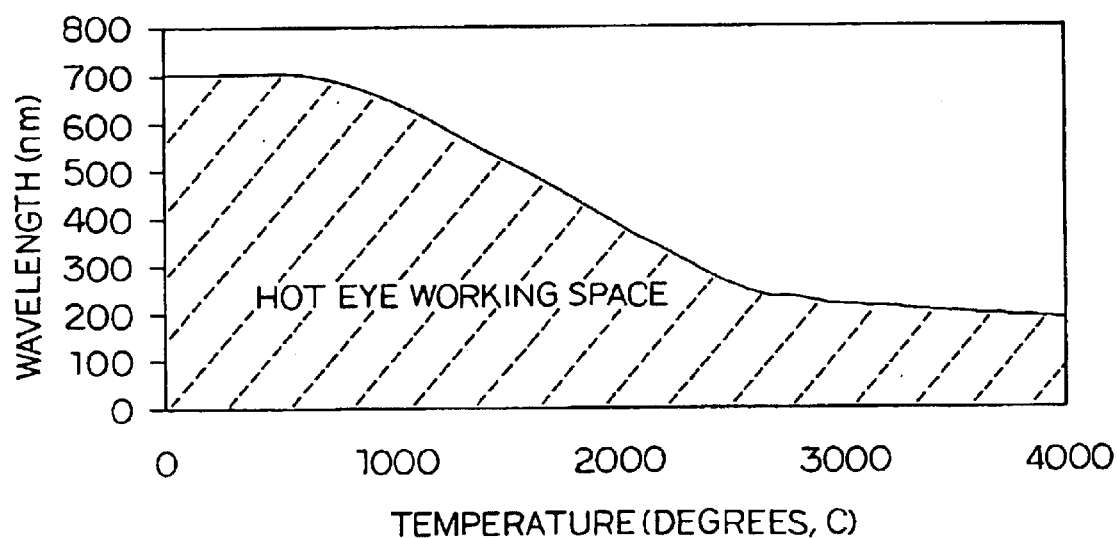
FIG. 2 is a graph illustrating the wavelengths used in the present invention to distinguish over the self-emitted radiation.

In this embodiment of the invention, the wavelength of reflected radiation 28 is chosen such that it is distinguishable by detector 30 from the wavelength of the predominant self-emitted radiation 22'. More specifically, and referring now to FIG. 2 of the drawings, the present invention provides an envelope of distinguishable applied illumination wavelengths as a function of the temperature of object 20. Accordingly, detector 30 senses or detects reflected illumination 28 which will have a wavelength under the curve. The preferred longest wavelength of reflected illumination 28 distinguishable from the self-emitted radiation (based on temperature) is set forth in Table 1 below:

| Temperature (° C.) | Longest Usable Wavelength (nm) for detection by sensor 30 |
|---|---|
| <800 | 700 nm |
| 800 | 680 |
| 1000 | 645 |
| 1200 | 596 |
| 1400 | 545 |
| 1600 | 596 |
| 1800 | 441 |
| 2000 | 385 |
| 2200 | 338 |
| 2400 | 283 |
| 2600 | 233 |
| 3000 | 220 |
| 4000 | 185 |

The wavelengths above are derived based on the assumption that object 20 is a blackbody radiator and will be suitable for all applications because the spectral radiation intensity emitted by a real surface at a given temperature of a specific wavelength is always less than that emitted by a black body at the same temperature and wavelength. In one embodiment of the present invention, the process for selecting the applicable illumination wavelength $\lambda_2$ (arrow 26) can be determined more precisely as follows (Ozisik (1985), *Heat Transfer—A Basic Approach*, McGraw-Hill):

1. Define the highest object Temperature T.
2. Define the object emissivity $\epsilon$(T, material) which is a function of object temperature and material.
3. Obtain the self-emitted radiation spectrum based on the black body radiation function:

$$I(\lambda, T) = \frac{2\pi c^2 h}{\lambda^5} \cdot \frac{1}{e^{hc/\lambda\kappa T} - 1} \tag{1}$$

and the material emissivity $\epsilon$(T) where:
Π=pi
C=light speed
h=Planck's constant
λ=wavelength
κ=Boltzmann constant
$\epsilon$=emissivity function of temperature, empirically obtained.

Together we have the radiation spectrum as:
(2) R(λ, T, material)=$\epsilon$(T, material)·I(λ, T)
If the material is known, Equation (2) can be reduced to
(3) R(λ, T)=$\epsilon$(T)·I(λ, T)
R(λ,T) can be plotted in general as the solid lines in FIG. 6. To further simplify, $\epsilon$(T) can typically be assumed to be a constant.

4. With R (λ, T), we can find a cut-off wavelength $\lambda_{cut\text{-}off}$ such that R($\lambda_{cut\text{-}off}$, T) is very small compared to the signal intensity of the external illuminating light $\eta(\lambda_{ill})$. Note that $\lambda_{ill}$ is typically a shorter wavelength than $\lambda_{cut-off}$.

$$\gamma = \frac{\eta(\lambda_{ill})}{R(\lambda_{cut-off}, T)} \geq \gamma_o \qquad (4)$$

where:
$\eta(\lambda)$=the intensity of the external illuminating light @ wavelength $\lambda$.
$\lambda_{ill}$=the wavelength used for external illumination.
$\gamma$=signal to noise ratio between the external illuminating light intensity and the self-emitted light intensity.
$\gamma_o$=specified signal to noise ratio limit that will satisfy the application.

$\eta(\lambda)$ is usually a function of the external illumination device. For instance, as stated above, a halite lamp has an $\eta(\lambda)$ like that seen in FIG. 6.

Accordingly, the longest acceptable wavelength for the projected (reflected) EMR is that at which a blackbody radiates a spectral radiance of $5\times10^{-4}$ W/cm$^2$.nm (i.e., power (in watts) per unit area per unit wavelength), at the highest temperature of the hot object at observation. Thus, I in equation (1) above becomes $5\times10^{-4}$ W/cm$^2$. By solving for $\lambda$ and where T equals the object's highest temperature at observation, the longest permissible wavelength for a given object which can be distinguished from the self-emitted radiation can be determined.

Figure 6:
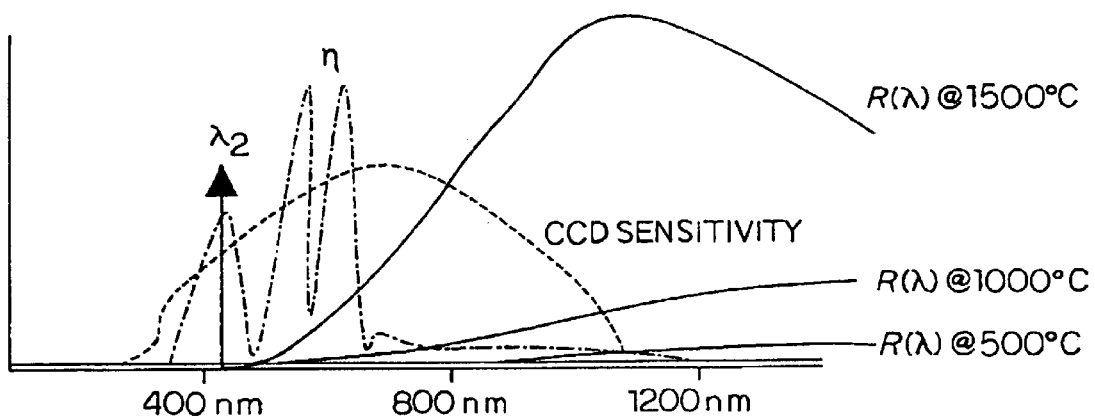
FIG. 6 is graph illustrating the selection of a desired wavelength.

Of course, the selection of $\lambda_{ill}$ has to satisfy the sensitivity spectrum of detecting sensor 30. For instance, a CCD is sensitive to the range seen in FIG. 6. $\lambda_{ill}$ should be a wavelength which sensor 30 can detect. The $\lambda_2$ in FIG. 6 is suitable for applications that are as hot as 1500° C.

Illumination source 24 may take a number of forms, but it must be capable of generating illumination which includes the required detectable wavelength. In other words, if a wavelength of 645 nm or less is required to distinguish reflected radiation 28 from self-emitted radiation 22', then illumination source 24 must include EMR at 645 nm or less. One acceptable illumination source 24 is a halite lamp which emits EMR principally at 435 nm, 550 nm and 575 nm. Other preferred "light" sources for illumination source 24 are fluorescent lamps and xenon lamps.

In the case of a laser illuminator, due to the coherent nature of the laser illumination, the wavelength of the laser should be set to the required wavelength in accordance with Table I above.

A laser can also be used herein as a point illumination source. Detector 30 can be used to detect information at the point illuminated by the laser. When coupled with a direction set, such as a mirror set, lasers can be used to create a raster-scanned image. Lasers in the present invention, through the use of certain optics such as a beam expander, can also be used as a zone illumination source, where the zones are relatively small.

Lasers can also be used with certain optics for structured illumination (circular lines, straight lines, single lines or multiple lines etc.). The structured illumination can be used to extract the profiles of hot objects in accordance with the present invention. Multiple lasers can be used for multiple points, lines, or zones.

Of course, the intensity of the EMR projected from illumination source 24 (and the distances between source 24, target 22 and detector 30) must be such that sufficient signal strength is present at detector 30.

Those skilled in the art will appreciate that this invention can be used in conjunction with other illumination methods, such as front lighting, bright field or dark field, and back lighting (transmissive lighting). The illumination can be collimated or scattered, monochromatic or color, structured or non-structured. Multiple illumination schemes can be applied.

It is also possible to have multiple wavelengths of reflected illumination 28 detected by detector 30 in a system, as long as all of the selected wavelengths meet the criteria.

Those skilled in the art will also understand that additional optics, such as, but not limited to, lenses, mirrors, optical fibers, diffusers, collimators, condensers, prisms, borescopes, endoscopes, and light guides, can be used in conjunction with the embodied designs. These optics can be used along with the illumination device (illuminating radiation source and modulator) to deliver the illumination onto the targeted hot object(s) for the purpose of illuminating multiple spots, or illuminating multiple objects, or any other intended illumination designs. These optics can also be used along with the signal collectors to receive the radiation signals from the hot object(s) for the purpose of meeting space constraints or to change the observation angles, for example.

Turning now to detector 30, a preferred detector is a CCD (charge coupled device) sensor. A CCD sensor is typically sensitive to wavelengths from 360 nm to 1000 nm. Some newer imaging sensors, such as blue enhanced CCD chips are sensitive to wavelengths from 175 nm to 1000 nm.

Of course, detector 30 must be able to detect the desired reflected illumination 28 wavelength. Preferably, an interference filter 32 blocks substantially all of the self-emitted EMR (and reflected EMR which is not at the desired imaging wavelength).

Figure 3:
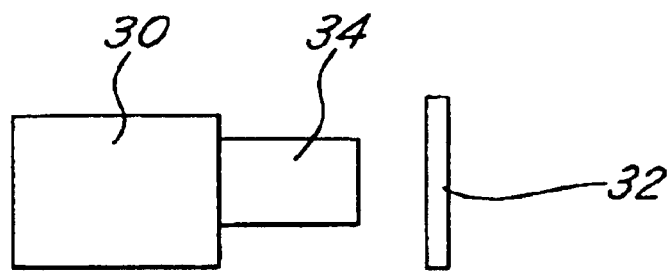
FIG. 3 is a diagram illustrating one possible arrangement of a camera and interference filter.
Figure 4:
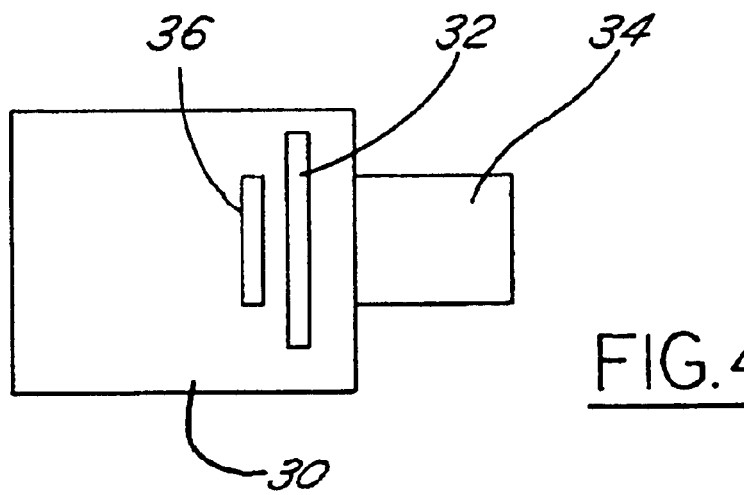
FIG. 4 is another diagram illustrating one possible arrangement of a camera and interference filter.
Figure 5:
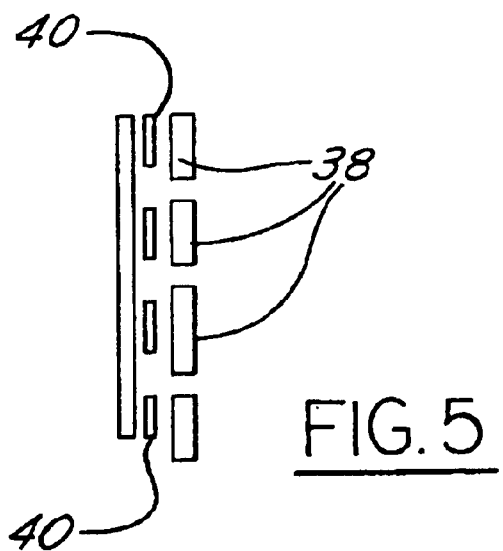
FIG. 5 is another diagram illustrating one possible arrangement of a camera and interference filter.

Interference filter 32 may be placed in front of the detector lens 34 as best shown in FIG. 3, or between lens 34 and imaging sensor 36 as shown in FIG. 4. It may also comprise multiple interference filters 38 in front of imaging sensor pixels 40 as shown in FIG. 5. Those skilled in the art can further perceive that the arrangement in FIG. 5 can be altered to facilitate the use of multiple illumination wavelengths. In this case, different interference filters 38, some working at one wavelength and some working at another, will be placed in front of pixels 40. With this arrangement, different pixels will be sensitive to the signals carried by different wavelengths. It is possible to have an aggregate of pixels, such as 2×3 or 3×1, within which each pixel is equipped with a different interference filter. This distribution is similar to that of a color CCD chip. It is also possible to have one type of interference filter installed in one zone of the imaging sensor while another type is installed in another zone.

It is also possible to facilitate the use of multiple wavelengths with multiple imaging sensors in a camera, with different interference filters in front of different imaging sensors. A prism is used to deliver optical radiations to all the imagine sensors. This arrangement is similar to that of a 3-chip CCD color camera.

Figure 7:
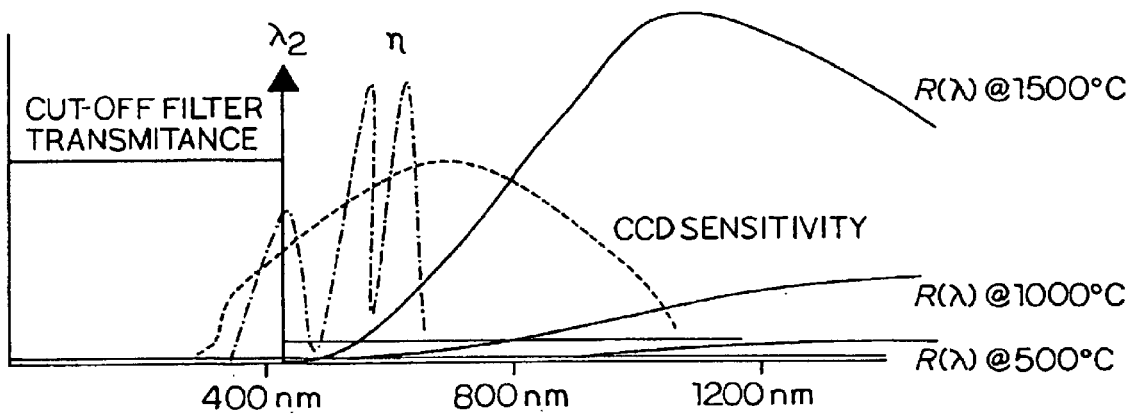
FIG. 7 is a graph illustrating the use of a cut-off filter in the present invention.

Those skilled in the art can also perceive the use of cut-off filters, instead of interference filters, in the application. The cut-off wavelength of the cut-off filter's transmittance curve must be at the desired wavelength. FIG. 7 illustrates the concept. With this setup, a single desired wavelength or multiple wavelengths can be used. In the case of multiple wavelengths, the signals carried by all the selected wavelengths will be treated as a combined signal.

Distortions in hot object imaging come from several sources. The above-described approach resolves the distortion influences of IR glare and Cavity Radiators. Another task is to creatively resolve the distortion associated with "mirage," the optical shimmering effect caused by localized air density non-uniformity. This is a common experience when one drives on a hot summer day. The road surface can appear to be "floating" and "wiggling." This "mirage" effect impairs the access to accurate measurements on hot objects through imaging.

In the present invention, controlled airflow 43 around hot object 20 decreases the temperature gradient around the hot object to remove air density distortion. Air flow 43 will be at a pre-selected temperature such that the temperature distribution of the hot object is not influenced adversely by such airflow. The speed of the airflow should be faster than about 0.01 m/s in order to avoid localized air density non-uniformity.

In another embodiment of the invention, and referring again to FIG. 1 of the drawings, signal modulator 42 is provided in order to place an identifiable "imprint" on applied illumination 26. In other words, in this embodiment of the invention the EMR from source 24 has an identifiable signature (other than merely wavelength) which allows reflected EMR 28 to be distinguished from self-emitted EMR 22'.

Figure 8:
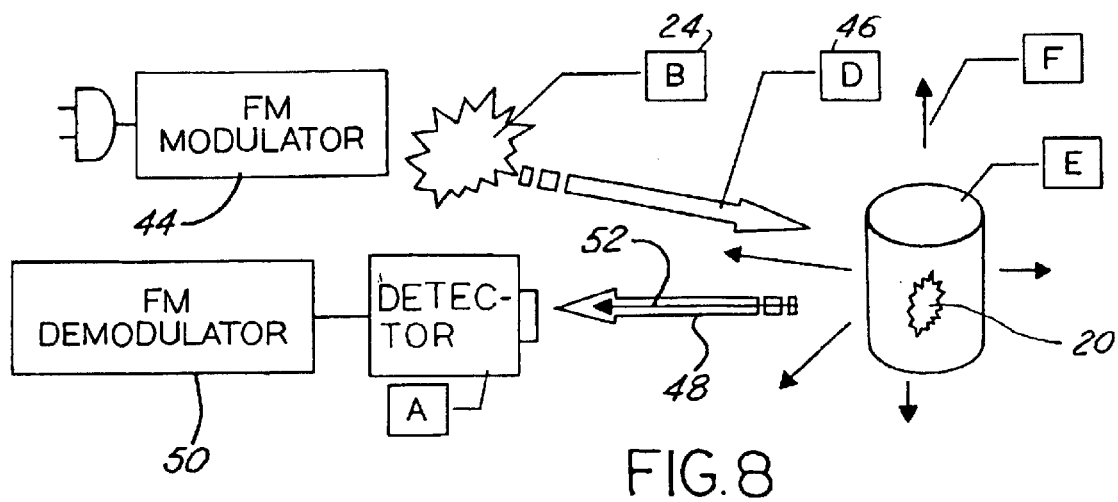
FIG. 8 is a graph illustrating the use of FM power modulation in the present invention.

A schematic of this implementation is also shown in FIG. 8. In this design, the power to illuminating source 24 is modulated through FM device 44. This FM signature will reside in the illuminating radiation 46 generated by source 24. The radiation is then projected onto the surface of hot object 20. The reflected signal 48 is received by imaging device 30 and then demodulated by FM demodulator 50 (through signal processing), based on the preset FM frequency, to remove the non-modulated radiation 52, i.e., the self-emitted radiation. The demodulation signal processing can be performed in hardware or software or by a combination of both. The frequency modulation can be a sequence of frequencies such that the applied (projected) radiation is the nature of repeating square waves or can be dynamic modulation, producing a sine wave of changing frequencies which can be detected and demodulated as a reflected radiation.

Figure 9:
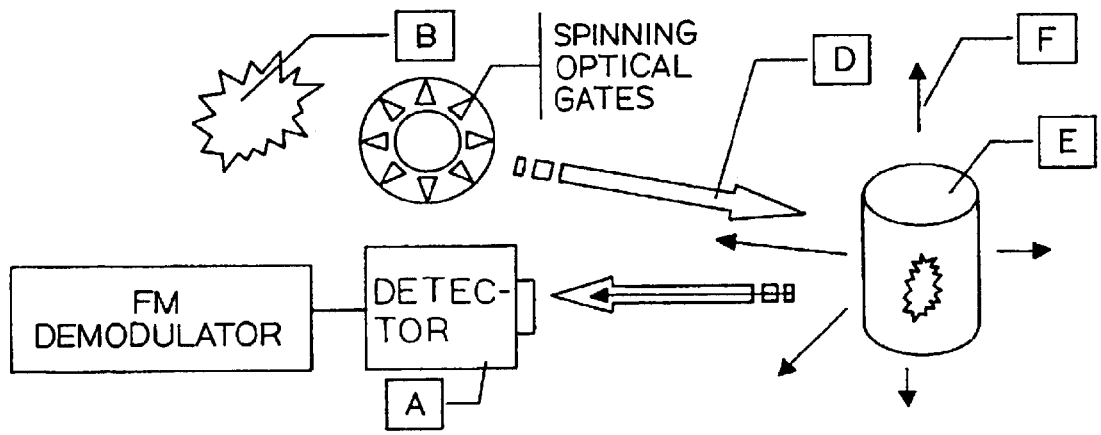
FIG. 9 is a graph illustrating the use of FM mechanical modulation in the present invention.

Modulation can also be implemented mechanically, with a mechanical gate to "pulse" the illuminating radiation, as illustrated in FIG. 9, or as a sine wave of intensity charges.

Devices which implement the embodied designs can be mobile, in part or as a whole. In one case the signal collector is mobile while the illumination device and hot object remain fixed. In another case the signal collector and the illumination device are both mobile and the hot object is stationary. It is also possible to move the hot object while the signal collector and the illumination device are stationary or mobile. It is also possible that two signal collectors or two illumination devices are used in one application, within which one is mobile and the other is stationary.

Figure 10:
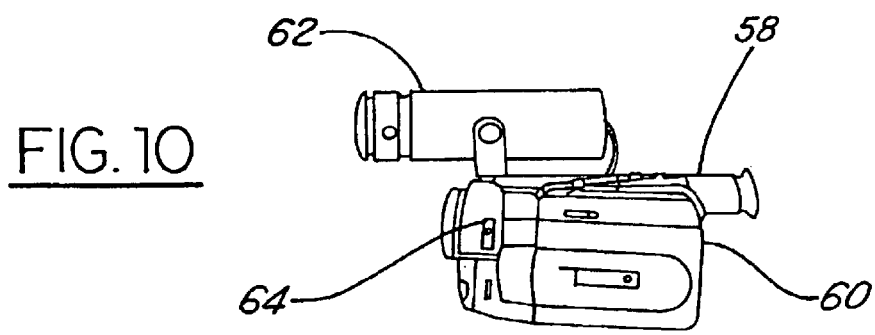
FIG. 10 is a drawing of a hand-held device in accordance with the present invention.

In still another embodiment, the present invention is implemented in the form of hand-held device 58. Referring now to FIG. 10 of the drawings, hand-held camcorder 60 is shown having projection light 62 and interference filter 64. Camcorder 60, which may be digital or analog, is used as the signal collector. Interference filter 64 (preferably at 435 nm) is placed in front of the lens. External projection light 62 provides the applied illumination and radiates with a significant intensity (at 435 nm in this example). Light 62 could be fixed to the surface of camcorder 60 or be separate to provide multiple illumination angles. Camcorder 60 could use a magnetic tape, RAM, or any other suitable data storage device, or the device could be used simply as a display monitor. The video signal can be exported to a TV, a monitor, or a PC. Hand-held device 58 could be battery operated or could operate through an AC. power supply. This device can be used to observe the hot processes or objects in accordance with the present invention, i.e. by projecting the desired illumination at a hot object and viewing the image (with the self-emitted radiation filtered out) with the camcorder.

In another implementation, multiple signal collectors, such as cameras, can be used in one system to provide multiple viewpoints of the hot object. The use of multiple cameras can facilitate stereo imaging, which provides a three-dimensional image of the hot object. Also, multiple cameras can be used for multiple wavelengths, with each camera demodulating the signal carried by one wavelength.

Figure 11:
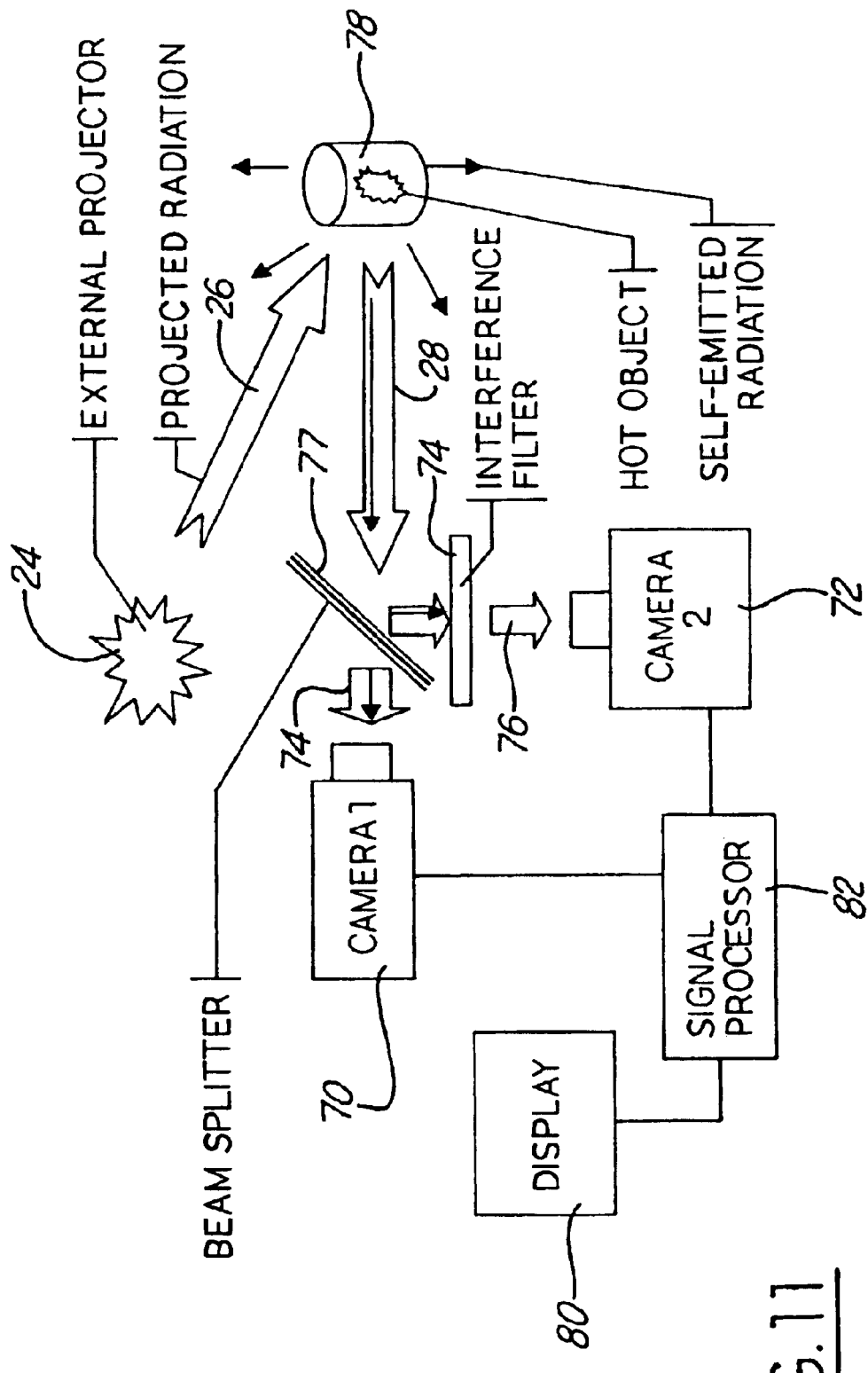
FIG. 11 is a schematic diagram of a two-camera embodiment of the present invention.

In another embodiment and referring now to FIG. 11, the invention can be used to protect individuals who must interact with hot objects. More specifically, in this design, two cameras 70,72 are used to capture the same field of view, with one capturing a normal image 74, which can be color or black/white, and the other capturing an image based on this invention 76 using beam splitter 77 and interference filter 79. In the normal image 74, hot object 78 is glowing. Glowing object 78 can be identified through a device, such as but not limited to, portable signal processor 82. With hot object 78 identified, the normal images of the glowing object can be replaced by room-temperature-appearance counterparts (cut out from 76 and pasted into 74). The synthesized image will be displayed to those who need to see everything in the field of view. Display 80 can be a monitor, a TV, or any other displaying device, including a displaying goggle. In order to identify the hot objects in the synthesized image, an indicator, such as, but not limited to, a red flashing boundary can be applied to the hot objects.

EXAMPLE

An example of the present invention in one embodiment is as follows:

1. The external illumination source is a halite lamp. The halite radiation consists of three principal wavelengths, 435 nm, 550 nm, and 575 nm. The radiation at 435 nm is the most useful wavelength in this design because it is the farthest one away from the self-emitted radiation of a hot object. The hot object must be at a temperature of 1800° C. or hotter for its self-emitted radiation to cover 435 nm, assuming the hot object is close to a black body.

2. The external radiation is projected onto the hot object and interacts with the surface of the hot object. The reflected radiation from the metal halite lamp (with all three distinct wavelengths), the self-emitted radiation from the hot object, and any other radiation present are all blended together.

3. The blended radiation is then passed through an interference filter, which has a working wavelength at 435 nm. That is, only the radiation at 435 nm wavelength can pas through this interference filter. All other radiation will be blocked. This interference filter can be placed in front of the lens, or in front of the imaging sensor.

4. Only radiation with the pre-selected wavelength, in this case 435 nm, can reach the imaging sensor.

5. The hot object will appear to the image sensor, say a CCD chip, as though it were at room temperature.

6. The demodulated 435 nm signal is then translated into an electronic signal.

7. The electronic signal may be processed by a CPU, stored to a media, displayed on a monitor for observation by a human or any other form of processing.

What is claimed is:

1. An optical system for producing an image of the surface of an object, said object having a characteristic, temperature-dependent, dominant, self-emitted EMR spectrum, comprising:
   an EMR source for projecting electromagnetic radiation toward said object;
   an EMR detector for selectively detecting a spectrum component of said projected EMR, said component being reflected by the surface of said object and being directed toward said EMR detector;
   an airflow controller to provide airflow at a preselected temperature around said hot object to decrease a temperature gradient to remove air density distortion; and
   wherein said projected electromagnetic radiation has a wavelength which is selected as a function of object temperature and material, said reflected component of said projected EMR has said wavelength that is different than said self-emitted, dominant EMR spectrum such that the reflected component can be distinguished from said self-emitted EMR based on wavelength and wherein said optical system further includes an interference filter in association with said EMR detector configured to pass said wavelength and block self-emitted EMR.

2. An optical system as recited in claim 1, further including a frequency modulator in association with said EMR source for modulating the frequency of said projected EMR and further including a demodulator in association with said EMR detector.

3. A method of imaging the surface of a hot object having a characteristic, dominant, self-emitted electromagnetic radiation (EMR) spectrum comprising the steps of:
   (A) defining a highest temperature, T, of the object during imaging;
   (B) defining an object emissivity $\epsilon$ (T, material) that is a function of the highest temperature T and material of the object;
   (C) obtaining a self-emitted electromagnetic radiation spectrum R ($\lambda$, T, material) based on a black body radiation function I($\lambda$, T), and the object emissivity $\epsilon$ (T) in accordance with R($\lambda$, T, material)=$\epsilon$(T, material) ·I($\lambda$, T) wherein:

$$I(\lambda, T) = \frac{2\pi c^2 h}{\lambda^5} \cdot \frac{1}{e^{hc/\lambda \kappa T} - 1}$$

and where
$\Pi$=pi
C=light speed
h=Planck's constant
$\lambda$=wavelength
$\kappa$=Boltzmann constant
$\epsilon$=emissivity function of temperature, empirically obtained, (D) selecting a cut-off wavelength $\lambda$ cut-off such that the self-emitted electromagnetic radiation spectrum R($\lambda_{cut-off}$,T) is small compared to a signal intensity of an external, illuminating light $\eta(\lambda_{ill})$, in accordance with:

$$\gamma = \frac{\eta(\lambda_{ill})}{R(\lambda_{cut-off}, T)} \geq \gamma_o$$

where:
$\eta(\lambda)$=the intensity of the external illuminating light @ wavelength $\lambda$
$\gamma_{ill}$=the wavelength used for external illumination
$\gamma$=signal to noise ratio between the external illuminating light intensity and the self-emitted light intensity
$\gamma_o$=specified signal to noise ratio limit that will satisfy the application (E) determining the longest acceptable wavelength $\gamma_{ill}$ for the external illumination;
(F) projecting light with a wavelength less than or equal to $\gamma_{ill}$ toward the hot object;
(G) detecting the projected light as reflected from the hot object to thereby image the hot object.

* * * * *